United States Patent [19]
Mower

[11] Patent Number: 6,141,586
[45] Date of Patent: Oct. 31, 2000

[54] METHOD AND APPARATUS TO ALLOW CYCLIC PACING AT AN AVERAGE RATE JUST ABOVE THE INTRINSIC HEART RATE SO AS TO MAXIMIZE INOTROPIC PACING EFFECTS AT MINIMAL HEART RATES

[75] Inventor: Morton M. Mower, Baltimore, Md.

[73] Assignee: Mower Family CHF Treatment Irrevocable Trust, Baltimore, Md.

[21] Appl. No.: 09/084,571

[22] Filed: May 26, 1998

Related U.S. Application Data

[63] Continuation-in-part of application No. 08/699,552, Aug. 8, 1996, Pat. No. 5,871,506.

[51] Int. Cl.$^7$ ................................................. A61N 1/362
[52] U.S. Cl. ................................................. 607/9; 607/14
[58] Field of Search .................................. 607/9, 14, 15, 607/122

[56] References Cited

U.S. PATENT DOCUMENTS

| | | | |
|---|---|---|---|
| 3,924,641 | 12/1975 | Weiss | 128/419 |
| 3,946,745 | 3/1976 | Hsiang-Lai et al. | 128/421 |
| 4,298,007 | 11/1981 | Wright et al. . | |
| 4,343,312 | 8/1982 | Cals et al. | 128/419 |
| 4,402,322 | 9/1983 | Duggan | 607/9 |
| 4,429,697 | 2/1984 | Nappholz et al. | 607/9 |
| 4,444,195 | 4/1984 | Gold | 607/122 |
| 4,498,478 | 2/1985 | Bourgeois | 128/419 |
| 4,503,857 | 3/1985 | Boute et al. . | |
| 4,545,956 | 10/1985 | Herscovoci | 128/419 |
| 4,903,700 | 2/1990 | Whigham et al. | 128/419 |
| 5,105,810 | 4/1992 | Collins et al. . | |
| 5,334,220 | 8/1994 | Sholder . | |
| 5,340,361 | 8/1994 | Sholder . | |
| 5,350,401 | 9/1994 | Levine . | |
| 5,423,868 | 6/1995 | Nappholz et al. . | |
| 5,441,522 | 8/1995 | Schüller . | |
| 5,480,413 | 1/1996 | Greenhut et al. . | |
| 5,514,163 | 5/1996 | Markowitz et al. . | |
| 5,527,347 | 6/1996 | Shelton et al. . | |
| 5,534,015 | 7/1996 | Kroll et al. | 607/7 |
| 5,545,186 | 8/1996 | Olson et al. . | |
| 5,601,608 | 2/1997 | Mouchawar | 607/5 |
| 5,626,620 | 5/1997 | Kieval et al. . | |
| 5,649,966 | 7/1997 | Noren et al. | 607/4 |
| 5,713,929 | 2/1998 | Hess et al. | 607/14 |
| 5,814,079 | 9/1998 | Kieval | 607/4 |
| 5,871,506 | 2/1999 | Mower | 607/9 |
| 5,968,081 | 10/1999 | Levine | 607/9 |

FOREIGN PATENT DOCUMENTS

| | | | |
|---|---|---|---|
| 0 491 649 A2 | 6/1992 | European Pat. Off. | A61N 1/39 |
| 0 600 631 A2 | 11/1993 | European Pat. Off. | A61N 1/368 |
| 0 813 889 A2 | 12/1997 | European Pat. Off. | A61N 1/368 |
| 2763247 | 5/1997 | France | A61N 1/365 |
| 93/01861 | 2/1993 | WIPO | A61N 1/36 |
| 97/25098 | 7/1997 | WIPO | A61N 1/00 |

*Primary Examiner*—Carl H. Layno
*Attorney, Agent, or Firm*—Roberts, Abokhair & Mardula LLC

[57] ABSTRACT

Method and apparatus for cyclic ventricular pacing starting at a rate just above the intrinsic atrial firing rate (overdrive pacing), followed by relaxation to a rate just below the intrinsic atrial firing rate (ventricular escape). The method and apparatus can be applied to one or both ventricles, and can utilize one or more electrodes per ventricle. The electrode(s) can be applied to inner or outer ventricular surfaces. Relaxation protocols as a function of time can be linear, curvilinear to include exponential, or mixtures thereof. Furthermore, relaxation protocols can include one or more periods of time during which the pacing rate is held constant. Typically, the average ventricular pacing rate using this invention will be slightly greater than the intrinsic atrial firing rate, though alternate embodiments that encompass average ventricular pacing rates that are equal to or slightly less than the intrinsic atrial firing rate are also envisioned. Application of this method and apparatus to a heart in need thereof will produce a heart with an optimally minimized energy output requirement.

28 Claims, 4 Drawing Sheets

METHOD AND APPARATUS TO ALLOW CYCLIC PACING AT AN AVERAGE RATE JUST ABOVE THE INTRINSIC HEART RATE SO AS TO MAXIMIZE INOTROPIC PACING EFFECTS AT MINIMAL HEART RATES

RELATED APPLICATION DATA

The present disclosure is a continuation-in-part application related to the U.S. patent application entitled "Augmentation of Electrical Conduction and Contractility by Biphasic Cardiac Pacing", application Ser. No. 08/699,552, filed Aug. 8, 1996, now U.S. Pat. No. 5,871,506.

FIELD OF THE INVENTION

The present invention relates generally to pacemakers to control the beating of hearts. In particular, the present invention relates to pacemakers used to promote, on a cyclic basis, ventricular tracking of atrial firing by overdriving ventricular pacing at a rate slightly over the intrinsic heart (atrial) rate, followed by gradual relaxation of the rate of ventricular stimulation to the point of decoupling of ventricular beating from atrial firing, especially in conjunction with ventricular synchronizing techniques such as biventricular pacing, biphasic pulsing, and/or multiple-site ventricular pacing.

BACKGROUND OF THE INVENTION

A–V blocks, encountered frequently in cardiac patients, arise when electrical impulses flowing from the SA node along the conduction bundles are delayed when they reach the A–V junction/A–V node. In some pathologies, if an A–V delay is sufficiently great, the ventricles will beat at their own intrinsic and slower rate. With A–V blocks in other pathologies, the ventricles can beat at a variable and/or intermittent rate, or ectopic foci can appear, potentially leading to life threatening ventricular fibrillation.

A variety of strategies have been employed for pacemakers to overcome the adverse physiological effects of A–V blocks. One such strategy is overdriving or overpacing, in which the pacemaker stimulates the ventricles at a faster rate than the atrial beating rate. A problem encountered with such strategies is that the atrial and ventricular beating can not be coordinated for optimal pumping efficiency. Another problem is that such fast ventricular pacing rates fatigue the heart because physiological and biochemical functioning generally are not optimized. Furthermore, such additional fatigue only imposes greater restraints on the already limited life style of the typical cardiac patient. Thus, the patient with an already weakened heart can be subjected to unnecessary overstimulation, and be stressed and further weakened as a result of application of current pacemaking protocols.

Patented technologies relating to overdriving pacing with subsequent relaxation of the pacing rate include U.S. Pat. No. 5,626,620 to Kieval. et al., which discloses a pacemaker stimulation protocol in which fusion and/or near fusion beats are detected by monitoring changes in the characteristics of the evoked QRS. The protocol is adjustable to allow selection of an acceptable percentage of fusion beats. When an unacceptable fusion percentage is measured, the A–V delay is automatically decreased to lead to a higher ventricular beating rate from the pacemaker's synchronous pace pulses (ventricular "capture"). Once ventricular capture is maintained for a predetermined time interval or number of cycles without an unacceptable rate of fusion, the A–V interval is incrementally increased to produce a beating rate toward the rate at which fusion had previously occurred. Upon again meeting an unacceptable fusion percentage, the A–V delay is automatically decreased, and the cycle continues so as to approximate the longest A–V interval (i.e., the slowest ventricular beating rate) consistent with avoiding fusion.

U.S. Pat. No. 5,527,347 to Shelton, et al. discloses a pacemaker ventricular stimulation protocol in which the A–V delay is slowly increased until fusion occurs, at which point the A–V delay is decreased slightly. The cycle is then repeated. Thus, the A–V delay is cyclically maintained in a small range of about that corresponding to fusion, to slightly lower values (i.e., higher ventricular beating rate).

U.S. Pat. No. 5,522,858 to van der Veen discloses a pacemaker stimulation protocol in which A–V delays are gradually decreased until ventricular tracking of atrial firing occurs. In particular, the ventricles are stimulated after the atrial depolarization impulse reaches the ventricles, but are not stimulated during the ventricular refractory period. The net effect is to decrease the prolonged A–V delay period, and thus increase the ventricular beating rate. In small increments, the A–V delay period then is further decreased until ventricular tracking is observed.

U.S. Pat. No. 5,480,413 to Greenhut, et al. discloses a means for using a pacemaker to correct ventricular beating rate instability in the presence of atrial fibrillation/tachyarrhythmia. First, ventricular beating is decoupled from atrial beating by gradually increasing the ventricular beating rate (dual or multichamber pacemakers are switched to a single chamber pacing mode) via appropriately spaced electrical stimulations. Once a stabilized beating rate is achieved at the higher ventricular beating rate, then the rate of ventricular stimulation is slowly decreased to the lowest rate that provides ventricular rate stability, and held at this rate until the atrial tachyarrhythmia/fibrillation disappears. Dual or multi-chamber (atria and ventricles) pacemaking is then resumed.

U.S. Pat. No. 5,441,522 to Schüller discloses a dual chamber pacemaker stimulation protocol in which the A–V interval is cycled between two values when retrograde conduction from ventricular stimulation renders the atria refractory to the normally timed stimulation by the pacemaker. When such a condition is sensed, the A–V interval is shortened to one value. Once a predetermined time or number of pulses has occurred, or once a spontaneous ventricular reaction is sensed within the shortened A–V interval, then the longer A–V interval is restored.

U.S. Pat. No. 5,340,361 to Sholder discloses a ventricular stimulation protocol in which the A–V interval is automatically adjusted to just less than that for the intrinsic (and pathological) rhythm to produce a ventricular firing that is slightly in advance of the intrinsic ventricular firing time. This invention overcomes the problem of abnormal A–V delay, which decreases cardiac efficiency due to non-optimal atrial-ventricular synchronization. The rates of atrial firing and ventricular firing are equal in this invention.

U.S. Pat. No. 5,334,220 to Sholder discloses a ventricular stimulation protocol in which the A–V interval is automatically adjusted to avoid ventricular stimulation at a time that would result in fusion (at the cross-over point) with the endogenous ventricular stimulation. A final A–V value is selected by incrementally adjusting the A–V interval until the crossover point is reached with respect to the R wave. The final A–V value that is set is based on the determined cross-over point, adjusted by a small margin. Thus, this procedure overdrives the intrinsic rhythm to ensure a suitably short A–V interval/delay that, otherwise, would impair cardiac pumping efficiency. When this procedure is invoked (automatically) too frequently, it is suspended for a predetermined period.

U.S. Pat. No. 5,105,810 to Collins, et al. discloses a cyclic protocol for achieving the minimum voltage for ventricular pacing for the purpose of extending the life of batteries used in pacemakers. The protocol uses a series of bradyeardia support pacing pulses at a predetermined voltage, and ventricular pressure measurements are analyzed during the pulse train to determine if capture has occurred. If capture has occurred during the pulse train, bradycardia support pacing pulses again are delivered once the stimulus voltage has been decreased by a step. If capture is the result, then the decremental voltage stepping and capture assessing is continued until capture is lost, at which point the voltage is incrementally increased until capture occurs.

U.S. Pat. No. 4,503,857 to Boute, et al. discloses a ventricular pacing protocol in which either spontaneous bradycardia or tachycardia is altered first by ventricular capture, followed by gradual increase or decrease, respectively, in the rate of pulse pacing until a normal programmed pacing rate is reached.

As can be seen from earlier inventions, pacemakers utilize overdrive ventricular pacing that adjusts the A–V interval/delay in a manner that avoids fusion, and that controls ventricular firing solely by the imposed pacing impulses. However, such protocols have not been optimally designed to minimize the energy expenditure of the already compromised patient's heart. Generally, the above references are designed to change the stimulation rate by adjustment of the A–V interval/delay in order to achieve a predetermined rate or a physiological standard.

What is needed is a pacemaker with a ventricular firing protocol that minimizes the energy of the heart used for contraction/pumping work. Furthermore, what is needed is a pacemaker with a ventricular firing protocol in which the maximum overdrive pacing rate is only slightly (i.e., only a few beats per minute—ideally two or three beats per minute) greater than the atrial firing rate at the commencement of the first cycle of the protocol. In addition, what is needed is a pacemaker for ventricular firing that uses a pacing protocol that achieves re-synchronization/fusion, so as to produce the least amount of stress on a heart which may already be in a weakened condition.

Lastly, an improved means for stimulating muscle tissue, wherein the contraction elicited is enhanced and the damage to the tissue adjacent to the electrode is diminished, is also desired. Enhanced myocardial function is obtained through the biphasic pacing of the present invention. The combination of cathodal with anodal pulses of either a stimulating or conditioning nature, preserves the improved conduction and contractility of anodal pacing while eliminating the drawback of increased stimulation threshold. The result is a depolarization wave of increased propagation speed. This increased propagation speed results in superior cardiac contraction leading to an improvement in blood flow. Improved stimulation at a lower voltage level also results in reduction in power consumption and increased life for pacemaker batteries.

SUMMARY OF THE INVENTION

It is therefore an object of the present invention to provide a pacemaker with a ventricular firing protocol that minimizes the energy required for contraction and pumping of the heart of a cardiac patient.

It is another object of the present invention to provide a pacemaker with a ventricular firing protocol that uses ventricular overdrive pacing only to a minimal degree; i.e., overdrive pacing is just a few beats per minute greater than the intrinsic atrial firing rate.

It is a further object of the present invention to provide a pacemaker with a ventricular firing protocol with a pacing relaxation period in which the ventricular pacing rate is slowly decreased to just slightly less (i.e., by only 1–2 beats per minute) than the intrinsic atrial firing rate before commencement of the next cycle.

It is a further object of the present invention to directly adjust the ventricular pacing cycle length, rather than the A–V delay.

It is a further object of the present invention to provide rate modulation in conjunction with multiple-site ventricular pacing.

The present invention accomplishes the above objectives by providing a ventricular firing protocol that is initiated by synchronization with the QRS complex of the electrocardiogram. The time from one QRS complex to the next constitutes a practical definition of the length of a heart beat, thereby providing the control circuit with a ready, strong reference point that serves as a timing mark for the timing of the firing trigger of the first electrical impulse to the ventricle(s). In theory, a P wave with an appropriate time interval could work. However, the weak P wave could disappear in the presence of conditions such as atrial fibrillation. This is particularly true in the case of pathological hearts. Therefore, the QRS complex, because of its large amplitude, serves as the best reference point available in the electrocardiogram. However, it is to be understood that the practice of the initial phase of this invention amounts to indirect timing/coordination with respect to atrial firing and contraction, as this is required for optimal total cardiac functioning.

The ventricular firing protocol is activated upon detection of a QRS complex, and is set at an overdrive rate of only a few beats per minute (i.e., no more than 3–5 beats per minute) greater than the intrinsic atrial firing rate. Next, the ventricular firing rate is slowly decreased ("relaxed") to a rate just a few beats per minute (i.e., no more than 2–3 beats per minute; ideally, only 1–2 beats per minute) below the intrinsic atrial firing rate, which leads to ventricular escape (i.e., atrial firing and contraction no longer coordinate perfectly with ventricular firing and contraction).

Subsequently, a new cycle is commenced.

Thus, the present invention uses a stimulation rate that is continuously cycled from a highest rate that is just barely above the intrinsic atrial firing rate, to a rate just barely below the intrinsic atrial firing rate. Such a stimulation protocol is expected a priori to provide a good approximation of an optimal lowest energy requiring protocol. Therefore, the limited energy of the cardiac patient can be used wisely and optimally to the benefit of the already compromised patient. In summary, this technique allows pacing at an average rate that is just above the intrinsic heart rate so as to maximize inotropic pacing effects at minimal heart rates, and thereby conserve the precious energy of the patient's heart.

Additionally, the ventricular firing protocol of the present invention can be used in conjunction with biphasic pacing. The method and apparatus relating to biphasic pacing comprises a first and second stimulation phase, with each stimulation phase having a polarity, amplitude, shape, and duration. In a preferred embodiment, the first and second phases have differing polarities. In one alternative embodiment, the two phases are of differing amplitude. In a second alternative embodiment, the two phases are of differing duration. In a third alternative embodiment, the first phase is in a chopped wave form. In a fourth alternative embodiment, the amplitude of the first phase is ramped. In a fifth alternative embodiment the first phase is administered over 200 milliseconds after completion of a cardiac beating/pumping cycle. In a preferred alternative embodiment, the first phase of stimulation is an anodal pulse at maximum subthreshold amplitude for a long duration, and the second phase of stimulation is a cathodal pulse of short duration and high amplitude. It is noted that the aforementioned alternative embodiments can be combined in differing fashions. It is also noted that these alternative embodiments are intended to be presented by way of example only, and are not limiting.

BRIEF DESCRIPTION OF THE DRAWINGS

FIG. 8 shows the use of multiple electrodes for applying pacing stimuli.

FIG. 9 is a flow chart for the sensing of physiological parameters.

DESCRIPTION OF THE PREFERRED EMBODIMENTS

Figure 1:
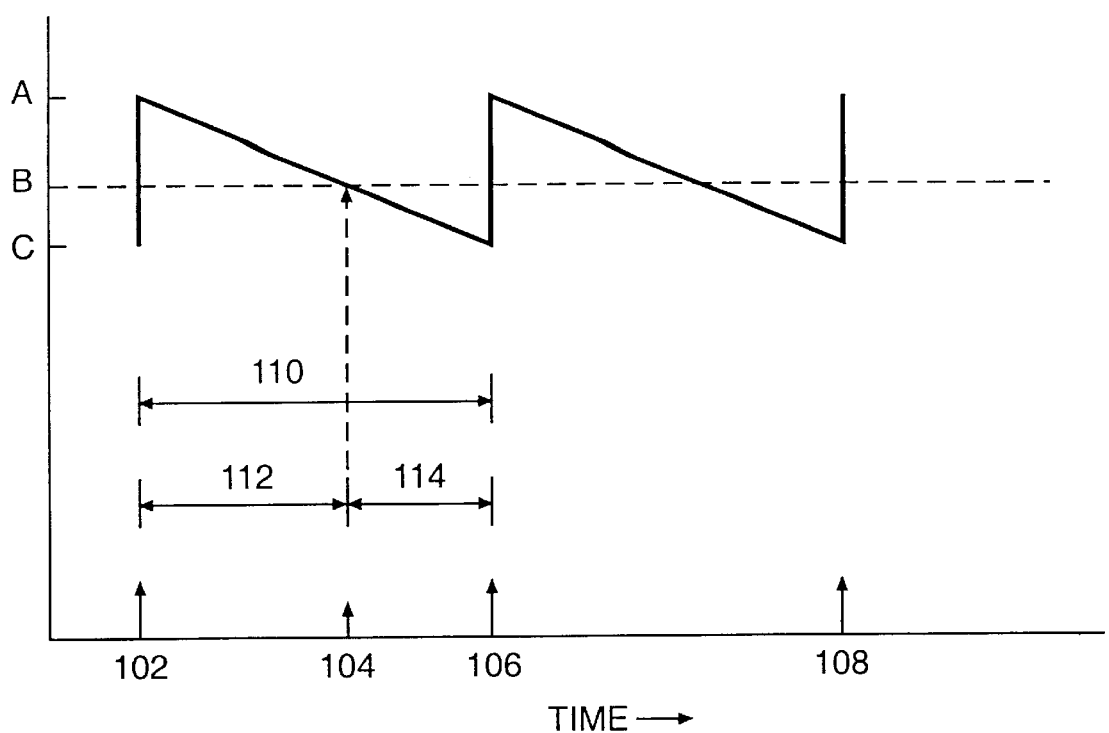
FIG. 1 shows a cyclic saw tooth (linear decay) stimulation-relaxation protocol for ventricular pacing.
Figure 2:
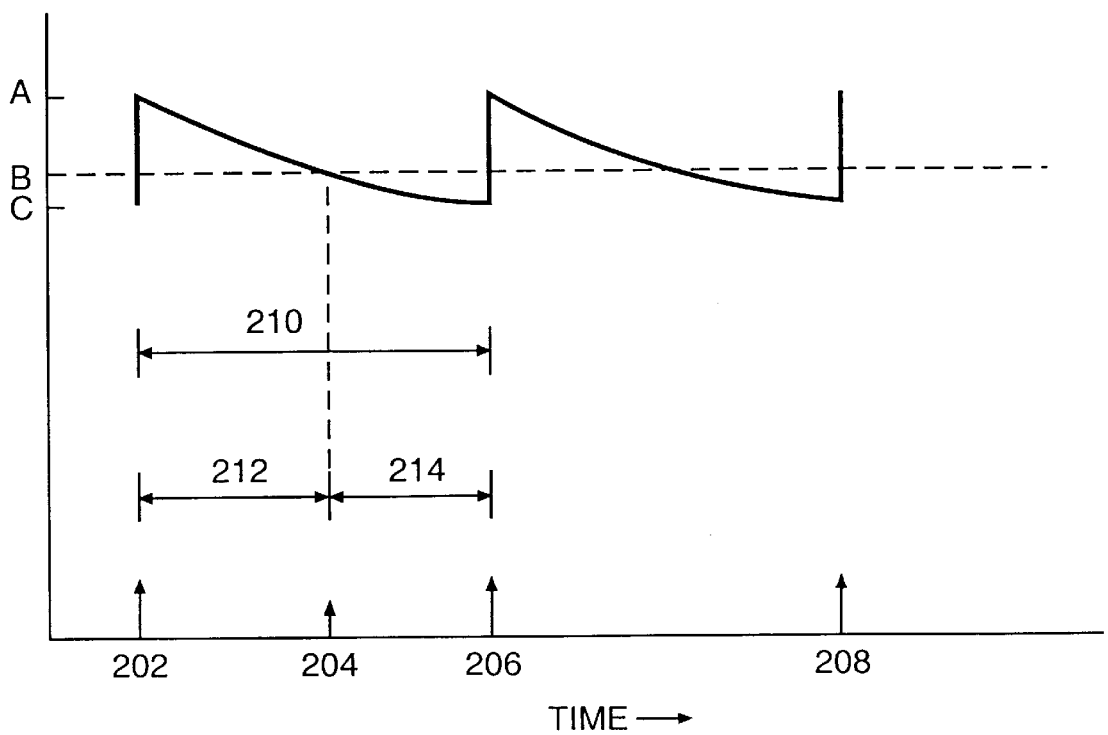
FIG. 2 shows a cyclic exponential decay stimulation-relaxation protocol for ventricular pacing.

The fundamentals of the present invention can be understood with reference to FIGS. 1 and 2, which depict two cyclic stimulation-relaxation protocols for ventricular pacing, in which the maximum rate of ventricular overdrive pacing is followed by relaxation to a rate just less than the intrinsic atrial firing rate (which corresponds to ventricular escape). FIG. 1 shows a cyclic saw tooth (linear decay) stimulation-relaxation protocol. FIG. 2 shows a cyclic exponential decay stimulation-relaxation protocol.

Referring to FIG. 1, a cyclic saw tooth stimulation-relaxation protocol for ventricular pacing is depicted with time points 102, 106, and 108 to illustrate initiation of ventricular overdrive pacing at maximum pacing rate A, followed by linear decay/relaxation of the rate of pacing to minimum pacing rate C. Each cycle has total time length 110. Intrinsic atrial firing rate B is shown as a dashed reference line. Rate difference A–B is greater than rate difference B–C in this example. B' illustrates the situation where A–B' is equal to B'–C. B" illustrates the situation where A–B" is less than B"–C. During the course of linear relaxation of the ventricular pacing rate, crossover point 104 is reached when the ventricular pacing rate equals intrinsic atrial firing rate B. Thus, the period between time point 102 and crossover point 104 represents linear ventricular overdrive pacing period 112, and the period between crossover point 104 and time point 106 represents linear ventricular escape period 114. It is evident that linear ventricular overdrive pacing period 112 is a longer time period than linear ventricular escape period 114. Therefore, the average ventricular firing rate for this protocol, with the above given relative parameters, will always be slightly greater than intrinsic atrial firing rate B.

Referring to FIG. 2, a cyclic exponential decay stimulation-relaxation ventricular pacing protocol is shown with ventricular overdrive pacing to maximum pacing rate A being initiated at time points 202, 206 and 208, followed by exponential relaxation of the rate of pacing to minimum pacing rate C. Each cycle has total time length 210. The time course of the pacing rate during the relaxation phase will be proportional to the time course of the product obtained by multiplying maximum pacing rate A (or the quantity A minus a selected "factor") by the proportionality $e^{1/\tau}$, where $\tau$ is the time constant. The selected "factor" typically will have a value less than C. As in FIG. 1, dashed line B represents the reference line of intrinsic atrial firing rate. Compared to FIG. 1, two parameters have been adjusted in FIG. 2. First, the relaxation of pacing rate is an exponential function of time instead of a linear function of time. Second, minimum ventricular pacing rate C is closer to intrinsic atrial firing rate B.

As in FIG. 1, the period between time point 202 and crossover point 204 represents exponential ventricular overdrive pacing period 212, and the period between crossover point 204 and time point 206 represents exponential ventricular escape period 214. Rate difference A–B is the same in FIGS. 1 and 2, as are cycle lengths 110 and 210. This combination of parameters produces a protocol in which exponential ventricular overdrive pacing period 212 of FIG. 2 is shorter than linear ventricular overdrive pacing period 112 of FIG. 1.

In the case of a curvilinear (including exponential) relaxation protocol with cycle length 210, comparison of ventricular overdrive pacing period 212 and ventricular escape period 214 of FIG. 2 reveals that their magnitudes effectively are controlled by variations in two parameters: (A–B)/(B–C), and ventricular overdrive pacing period 212.

Referring again to FIG. 1, in the case of a linear relaxation protocol with cycle length 110, comparison of linear ventricular overdrive pacing period 112 and linear ventricular escape period 114 reveals that their magnitudes are controlled by variation in single parameter (A–B)/(B–C), or any mathematical equivalent, such as (102–104)/(104–106).

It is anticipated that different relaxation protocols will be required for different pathologies and different medical situations. In addition, a virtually infinite array of relaxation protocols are possible in theory. Thus, the preferred embodiment of the present invention contemplates any monotonic relaxation protocol, where "monotonic" indicates a unidirectional change in the applied ventricular pacing rate. Further, "unidirectional change" is to be understood to refer to a change in ventricular pacing rate that is in the direction of decreasing ventricular pacing rate, and to include periods of time in which there is no change in ventricular pacing rate.

Therefore, the preferred embodiment of the present invention contemplates relaxation protocols beyond the two depicted in FIGS. 1 and 2, as long as the relaxation protocol embodies unidirectional change in ventricular pacing rate as defined above. Thus, the shapes of the relaxation curves can generally be decreasing linear, decreasing curvilinear, decreasing in an exponential fashion, include one or more periods at a constant pacing rate, or combinations of these. For example, with reference to FIG. 1, one can imagine a protocol in which, between time points 102 and 104, there is a small time segment over which the voltage is constant, followed by linear relaxation at the same or a different rate of relaxation (i.e., the same or a different slope) compared to the initial rate of relaxation. In one embodiment, the same or different rate of relaxation that follows the brief period of constant voltage is maintained up to time point 106, which marks the end of one cycle and the beginning of the next cycle.

Alternate embodiments encompass relaxation protocols in which ventricular pacing rates are not monotonic; i.e., as the ventricular pacing rate is declining in a given cycle, time periods in which the ventricular pacing rates are increased slightly can be included. Further alternative embodiments can include the use of combinations of different rates of relaxation within a single cycle, for example, within time segment 102–106, or 202–206.

Typically, as shown in FIG. 9, physiological data from one or more sensing electrodes (including electrodes that perform both pacing and sensing) are used to determine whether an "action criterion" has been met, in order to initiate a cyclic pacing protocol if the situation so demands. Such sensing may be directed to detecting such nonlimiting physiological parameters as abnormal or unacceptably long A–V delays, whether atrial firing entrains both left and right ventricles, length of the QRS complex, magnitude of the QRS complex, heart rate, arterial and/or venous blood pressure, ventricular fibrillation, atrial fibrillation, and probability density function ("PDF"). At the end of such a cyclic pacing protocol, sensing again is performed to determine if additional pacing is required. Alternatively, sensing can be conducted concurrently with a cyclic pacing protocol.

The ventricular firing protocol is activated upon detection of a QRS complex, and is set at an overdrive rate of only a few beats per minute (i.e., no more than 3–5 beats per minute) greater than the intrinsic atrial firing rate. Next, the ventricular firing rate is slowly decreased ("relaxed") to a rate just a few beats per minute (i.e., no more than 2–3 beats per minute; ideally, only 1–2 beats per minute) below the intrinsic atrial firing rate, which leads to ventricular escape (i.e., atrial firing and contraction no longer coordinate perfectly with ventricular firing and contraction). Heart rates could vary from about 40 to 120 beats per minute, with these rates being largely determined by the intrinsic physiology of the heart. Rates that vary greatly from this 40 to 120 beats per minute range would not be beneficial physiologically.

What is central to the present invention is that the ventricular pacing rates hover not far from the intrinsic atrial firing rate so as to minimize the energy requirements of the myocardium. Generally, practice of the present invention will result in an average ventricular beating rate that is just slightly greater than the intrinsic atrial firing rate. However, it is anticipated that some pathological/medical conditions will minimize the cardiac energy requirements with a relaxation protocol that results in an average ventricular beating rate that is equal to, or just slightly less than, the intrinsic atrial firing rate; and such relaxation protocols are well within the scope of the present invention.

The application of cyclic ventricular pacing with any of the above range of relaxation protocols pertains not only to mono-ventricular pacing, but also to biventricular pacing, and/or pacing from multiple sites as shown in FIG. 8. In the case of biventricualr pacing, right and left ventricles can be cyclically paced either on the same or similar time protocol or independently of one another. Furthermore, one pacing electrode or multiple pacing electrodes 800 can be employed per ventricle, and the pacing electrodes can be applied to the external surfaces of the ventricles and/or to the internal surfaces. Typically, internal pacing electrodes will be applied via the vena cava and the right atrium to the right ventricle only; however, multiple internal pacing electrodes are also contemplated for the left ventricle.

Additional embodiments encompass the use of monophasic stimulation, as well as biphasic stimulation. Furthermore, the monophasic stimulation and the biphasic stimulation can be applied to either atria or ventricles. Monophasic stimulation can be either cathodal or anodal, and is known to those skilled in the art. Biphasic cardiac stimulation is disclosed in U.S. patent application Ser. No. 08/699,552, now U.S. Pat. No. 5,871,506 to Mower, which is hereby incorporated by reference in its entirety.

Typically, a cyclic pacing/relaxation period will fall within the three to 30 second range; however, longer periods also are contemplated, particularly for patients with more "difficult" pathologies.

Figure 3:
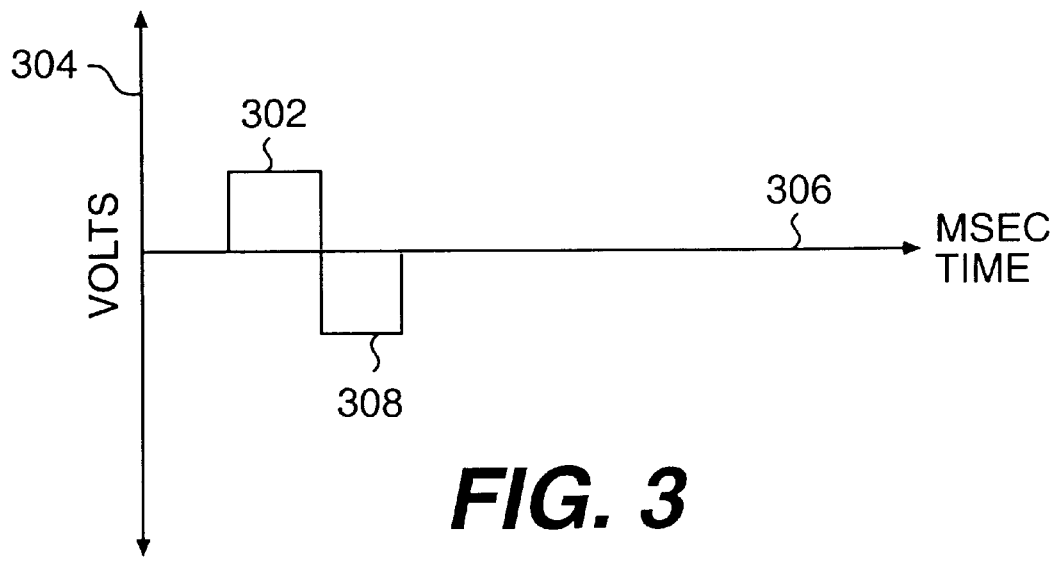
FIG. 3 is a schematic representation of leading anodal biphasic stimulation.

FIG. 3 depicts biphasic electrical stimulation wherein a first stimulation phase, comprising anodal stimulus 302, is administered having amplitude 304 and duration 306. This first stimulation phase is immediately followed by a second stimulation phase comprising cathodal stimulation 308 of equal intensity and duration.

Figure 4:
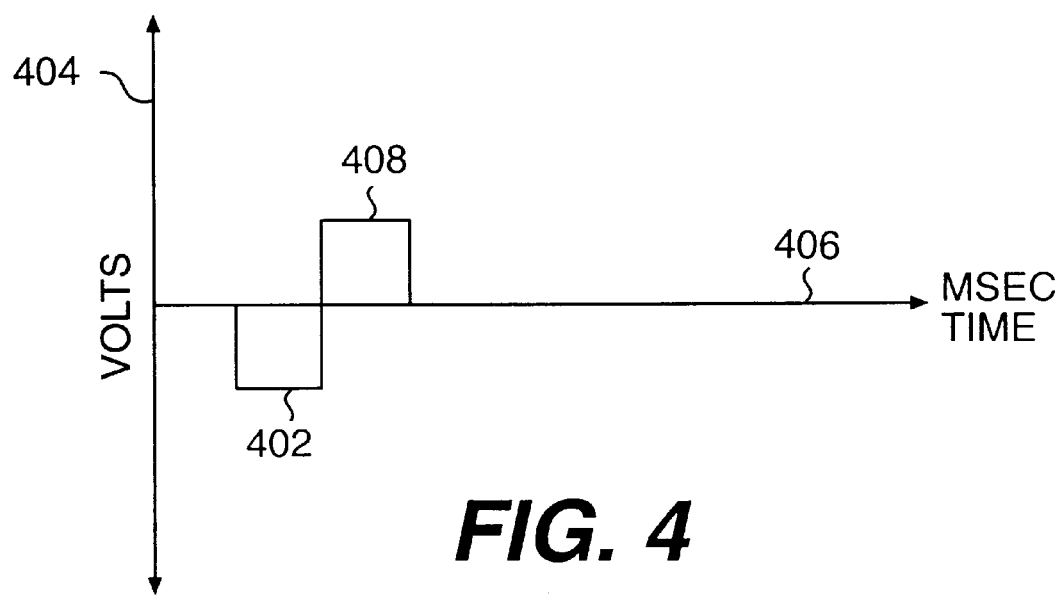
FIG. 4 is a schematic representation of leading cathodal biphasic stimulation.

FIG. 4 depicts biphasic electrical stimulation wherein a first stimulation phase, comprising cathodal stimulation 402 having amplitude 404 and duration 406, is administered. This first stimulation phase is immediately followed by a second stimulation phase comprising anodal stimulation 408 of equal intensity and duration.

Figure 5:
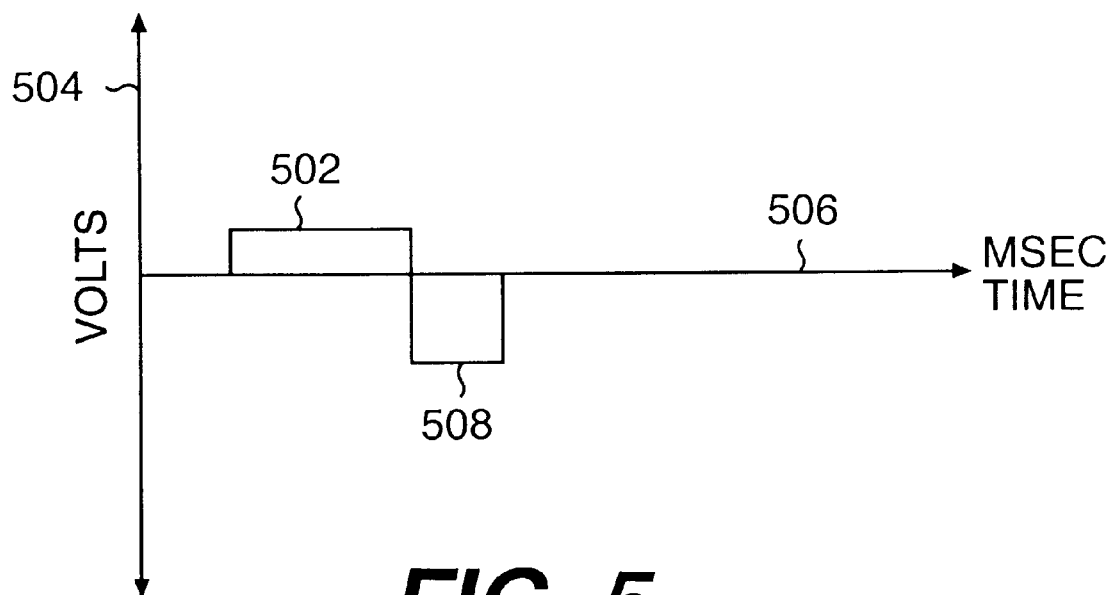
FIG. 5 is a schematic representation of leading anodal stimulation of low level and long duration, followed by cathodal stimulation.

FIG. 5 depicts a preferred embodiment of biphasic stimulation wherein a first stimulation phase, comprising low level, long duration anodal stimulation 502 having amplitude 504 and duration 506, is administered. This first stimulation phase is immediately followed by a second stimulation phase comprising cathodal stimulation 508 of conventional intensity and duration. In differing alternative embodiments, anodal stimulation 502 is: 1) at maximum subthreshold amplitude; 2) less than three volts; 3) of a duration of approximately two to eight milliseconds; and/or 4) administered over 200 milliseconds post heart beat. Maximum subthreshold amplitude is understood to mean the maximum stimulation amplitude that can be administered without eliciting a contraction. In differing alternative embodiments, cathodal stimulation 508 is: 1) of a short duration; 2) approximately 0.3 to 1.5 milliseconds; 3) of a high amplitude; 4) in the approximate range of three to twenty volts; and/or 5) of a duration less than 0.3 millisecond and at a voltage greater than twenty volts. In a preferred embodiment, cathodal stimulation is about 0.8 millisecond. In the manner disclosed by these embodiments, as well as those alterations and modifications which can become obvious upon the reading of this specification, a maximum membrane potential without activation is achieved in the first phase of stimulation.

Figure 6:
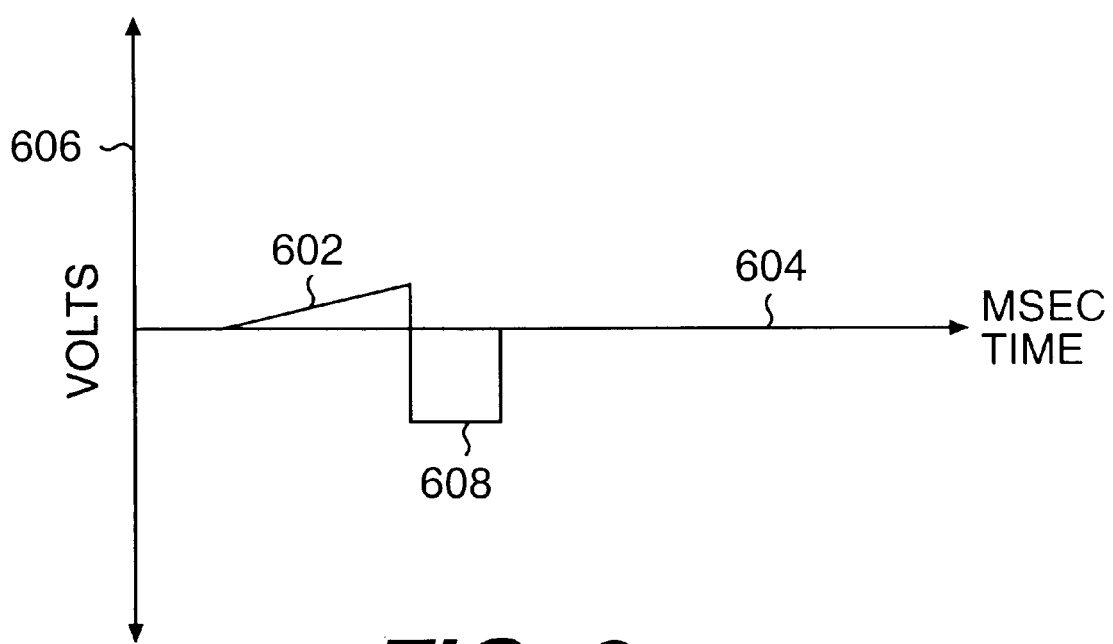
FIG. 6 is a schematic representation of leading anodal stimulation of ramped low level and long duration, followed by cathodal stimulation.

FIG. 6 depicts an alternative preferred embodiment of biphasic stimulation wherein a first stimulation phase, comprising anodal stimulation 602, is administered over period 604 with rising intensity level 606. The ramp of rising intensity level 606 can be linear or non-linear, and the slope can vary. This anodal stimulation is immediately followed by a second stimulation phase comprising cathodal stimulation 608 of conventional intensity and duration. In alternative embodiments, anodal stimulation 602: (1) rises to a maximum subthreshold amplitude less than three volts; (2) is of a duration of approximately two to eight milliseconds; and/or (3) is administered over 200 milliseconds post heart beat. In yet other alternative embodiments, cathodal stimulation 608 is: (1) of a short duration; (2) approximately 0.3 to 1.5 milliseconds; (3) of a high amplitude; (4) in the approximate range of three to twenty volts; and/or (5) of a duration less than 0.3 milliseconds and at a voltage greater than twenty volts. In the manner disclosed by these embodiments, as well as those alterations and modifications which can become obvious upon the reading of this specification, a maximum membrane potential without activation is achieved in the first phase of stimulation.

Figure 7:
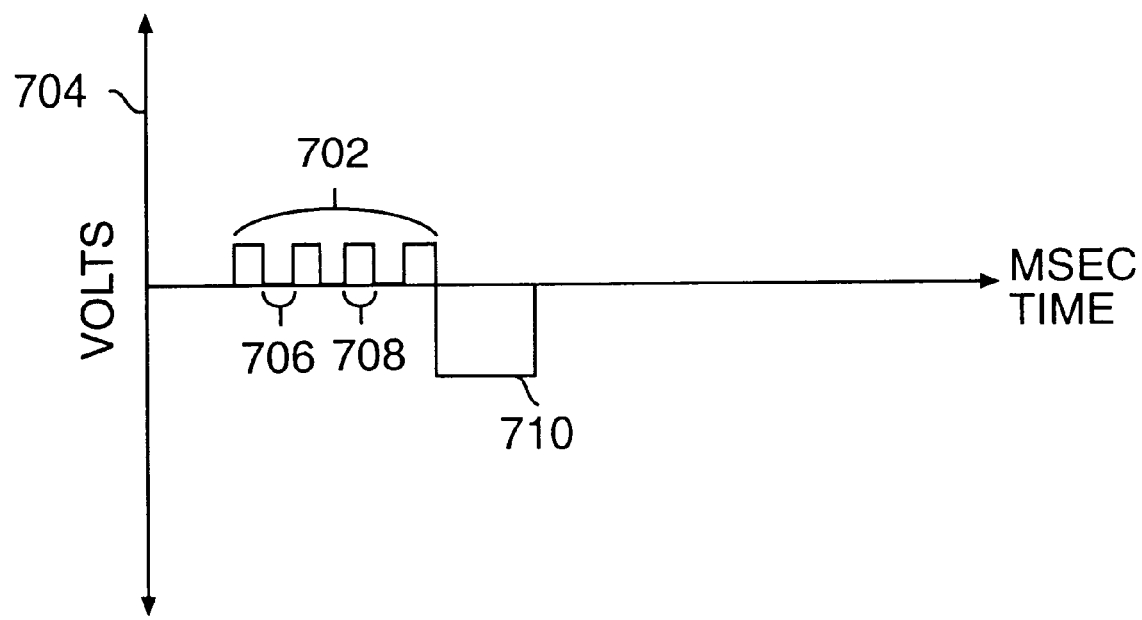
FIG. 7 is a schematic representation of leading anodal stimulation of low level and short duration administered in a series, followed by cathodal stimulation.

FIG. 7 depicts biphasic electrical stimulation wherein a first stimulation phase, comprising series 702 of anodal pulses, is administered at amplitude 704. In one embodiment, rest period 706 is of equal duration to stimulation period 708, and is administered at baseline amplitude. In an alternative embodiment, rest period 706 is of a differing duration than stimulation period 708, and is administered at baseline amplitude. Rest period 706 occurs after each stimulation period 708, with the exception that a second stimulation phase, comprising cathodal stimulation 710 of conventional intensity and duration, immediately follows the completion of series 702. In alternative embodiments: (1) the total charge transferred through series 702 of anodal stimulation is at the maximum subthreshold level; and/or (2) the first stimulation pulse of series 702 is administered over 200 milliseconds post heart beat. In yet other alternative embodiments, cathodal stimulation 710 is: (1) of a short duration; (2) approximately 0.3 to 1.5 milliseconds; (3) of a high amplitude; (4) in the approximate range of three to twenty volts, and/or (5) of a duration less than 0.3 milliseconds and at a voltage greater than twenty volts.

The preferred practice of the present invention is directed to ventricular pacing where the pacing rate skirts just above and below the intrinsic atrial pacing rate, and is timed (albeit indirectly) relative to intrinsic atrial firing in order to achieve optimal coordinated cardiac function. However, situations can be anticipated in which ventricular pacing is effected independently of intrinsic atrial firing.

Furthermore, when atrial rhythmicity is pathologic, the present invention can be practiced with respect to the rhythmicity of pacemaker paced atria. In embodiments in which atria are paced by extrinsic pacemakers, the clinical practitioner first sets the rate of atrial pacing, which can be fixed, or can be variable to permit appropriate response to changes in physical activity or other change which would require a change in heart rate, for example, an increased heart rate during a period of fever. Second, the ventricular firing protocol is selected according to the principles described and disclosed herein. It is to be emphasized that selection of the ventricular firing protocol generally will be a decision that is made independently of the atrial beating pattern, whether the atrial beating pattern is set intrinsically or extrinsically, for example, by a pacemaker. However, it is within the scope of the present invention to apply the teachings herein to cases in which decisions regarding extrinsically controlled atrial and ventricular beating protocols are considered in a linked, integrated manner.

In addition, testing procedures can be applied to achieve optimal parameters for a given patient with a particular constellation of pathologies. Thus, it is within the scope of the present invention to test, and vary, alternative stimulation pulse waveforms, for example, durations, amplitudes, and shapes of the various waveforms required to reach optimal physiological parameters for a particular patient at a given time. Further, various measurable parameters may be used to assess the effects of changes in stimulus waveforms, for example, the effects on pulse pressure, duration of the QRS complex, maximum fusion, and production of a minimal intrinsic heart rate, to name but a few.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Accordingly, the invention is limited only by the following claims and equivalents thereto.

What is claimed is:

1. A method for cardiac pacing for a heart having an intrinsic atrial firing rate, comprising:

applying a series of pacing stimuli to at least one ventricle having an initial pacing rate, where the initial pacing rate is slightly greater than the intrinsic atrial firing rate; and decreasing the pacing rate over time from the initial pacing rate to a minimum pacing rate that is slightly less than the intrinsic atrial firing rate.

2. The method for cardiac pacing according to claim 1, further comprising sensing physiological parameters to determine if additional cardiac pacing is needed.

3. The method for cardiac pacing according to claim 2, where the physiological parameters are selected from the group consisting of A–V interval, atrial entrainment of left and right ventricles, length of QRS complex, magnitude of QRS complex, arterial blood pressure, venous blood pressure, heart rate, ventricular fibrillation, atrial fibrillation, and probability density function.

4. The method for cardiac pacing according to claim 1, where applying the pacing stimuli and decreasing the pacing rate is repeated in a cyclic pattern.

5. The method for cardiac pacing according to claim 1, where a protocol for decreasing the pacing rate over time is selected from the group consisting of linear, curvilinear, exponential, and combinations thereof.

6. The method for cardiac pacing according to claim 5, where the protocol for decreasing the pacing rate includes one or more periods of time in which the pacing rate is held constant.

7. The method for cardiac pacing according to claim 1, where a protocol for decreasing the pacing rate includes one or more periods of time in which the pacing rate is held constant.

8. The method for cardiac pacing according to claim 1, where the initial pacing rate minus the intrinsic atrial firing rate is greater than the intrinsic atrial firing rate minus the minimum pacing rate.

9. The method for cardiac pacing according to claim 1, where the initial pacing rate minus the intrinsic atrial firing rate is equal to the intrinsic atrial firing rate minus the minimum pacing rate.

10. The method for cardiac pacing according to claim 1, where the initial pacing rate minus the intrinsic atrial firing rate is less than the intrinsic atrial firing rate minus the minimum pacing rate.

11. The method for cardiac pacing according to claim 1, where the pacing stimuli are selected from the group consisting of monophasic stimulation and biphasic stimulation.

12. The method for cardiac pacing according to claim 11, where the monophasic stimulation is selected from the group consisting of cathodal stimulation and anodal stimulation.

13. The method for cardiac pacing according to claim 11, where the biphasic stimulation comprises an anodal stimulation phase followed by a cathodal stimulation phase.

14. The method for cardiac pacing according to claim 13, where the anodal stimulation phase:

has a magnitude equal to or less than a maximum sub-threshold amplitude; and has an approximate shape selected from the group consisting of square wave, increasing ramp, and series of short duration square waves.

15. The method for cardiac pacing according to claim 1, where the pacing stimuli are applied via multiple electrodes to at least one ventricle.

16. A method for cardiac pacing for a heart with a paced atrial firing rate, comprising:

applying a series of pacing stimuli to at least one ventricle, where the initial ventricular pacing rate is slightly greater than the paced atrial firing rate; and decreasing the initial ventricular pacing rate over time to a minimum pacing rate that is slightly less than the paced atrial firing rate.

17. The method for cardiac pacing according to claim 16, wherein applying the pacing stimuli and decreasing the pacing rate is repeated in a cyclic pattern.

18. The method for cardiac pacing according to claim 16, where a protocol for decreasing the initial ventricular pacing rate over time is selected from the group consisting of linear, curvilinear, exponential, and combinations thereof.

19. The method for cardiac pacing according to claim 18, where the protocol for decreasing the initial pacing rate includes one or more periods of time in which the pacing rate is held constant.

20. The method for cardiac pacing according to claim 16, where a protocol for decreasing the pacing rate includes one or more periods of time in which the pacing rate is held constant.

21. The method for cardiac pacing according to claim 16, where the initial ventricular pacing rate minus the paced atrial firing rate is greater than the paced atrial firing rate minus the minimum ventricular pacing rate.

22. The method for cardiac pacing according to claim 16, where the initial ventricular pacing rate minus the paced atrial firing rate is equal to the paced atrial firing rate minus the minimum ventricular pacing rate.

23. The method for cardiac pacing according to claim 16, where the initial ventricular pacing rate minus the paced atrial firing rate is less than the paced atrial firing rate minus the minimum ventricular pacing rate.

24. The method for cardiac pacing according to claim 16, where the pacing stimuli are selected from the group consisting of monophasic stimulation and biphasic stimulation.

25. The method for cardiac pacing according to claim 24, where the monophasic stimulation is selected from the group consisting of cathodal stimulation and anodal stimulation.

26. The method for cardiac pacing according to claim 24, where the biphasic stimulation comprises an anodal stimulation phase followed by a cathodal stimulation phase.

27. The method for cardiac pacing according to claim 26, where the anodal stimulation phase:

has a magnitude equal to or less than a maximum sub-threshold amplitude; and has an approximate shape selected from the group consisting of square wave, increasing ramp, and series of short duration square waves.

28. The method for cardiac pacing according to claim 16, where the pacing stimuli are applied via multiple electrodes to at least one ventricle.

* * * * *